(12) United States Patent
Tatum et al.

(10) Patent No.: US 7,785,247 B2
(45) Date of Patent: Aug. 31, 2010

(54) PHYSIOLOGIC PULSATILE PUMP

(75) Inventors: Tani Tatum, Bishop, CA (US); Stephen Walker, Henderson, NV (US); Bob Wilson, Bishon, CA (US)

(73) Assignee: Medical Engineering Co., LLC, Bishop, CA (US)

(*) Notice: Subject to any disclaimer, the term of this patent is extended or adjusted under 35 U.S.C. 154(b) by 588 days.

(21) Appl. No.: 11/788,585

(22) Filed: Apr. 20, 2007

(65) Prior Publication Data

US 2008/0262288 A1      Oct. 23, 2008

(51) Int. Cl.
*A61H 31/00* (2006.01)
*A61M 1/10* (2006.01)

(52) U.S. Cl. .................. 600/16; 604/4.01; 422/44; 422/45

(58) Field of Classification Search .......... 604/1–10; 422/44–45; 600/16, 151, 5.01, 6.11, 6.14, 600/18; 417/43, 423.7, 383, 356, 412, 478; 623/3.1, 3.17, 3.24
See application file for complete search history.

(56) References Cited

U.S. PATENT DOCUMENTS

| | | | | |
|---|---|---|---|---|
| 3,814,547 A | * | 6/1974 | Kitrilakis et al. | 417/383 |
| 4,360,324 A | | 11/1982 | Ohara et al. | |
| 4,369,530 A | * | 1/1983 | Robinson et al. | 623/3.24 |
| 5,044,901 A | | 9/1991 | Fumero et al. | |
| 5,171,207 A | * | 12/1992 | Whalen | 600/16 |
| 5,360,445 A | * | 11/1994 | Goldowsky | 623/3.22 |
| 5,820,579 A | * | 10/1998 | Plotkin | 604/5.01 |
| 6,607,368 B1 | * | 8/2003 | Ross et al. | 417/412 |
| 7,189,352 B2 | * | 3/2007 | Carpenter et al. | 422/45 |
| 2005/0234287 A1 | * | 10/2005 | Weatherbee | 600/16 |
| 2008/0064917 A1 | * | 3/2008 | Bar et al. | 600/16 |

* cited by examiner

*Primary Examiner*—Carl H Layno
*Assistant Examiner*—Paula J Stice (57) ABSTRACT

A pulsatile blood circulating pump system that is adapted for use in cardiopulmonary bypass, ventricular assist (LVAD, RVAD, BiVAD), ECMO, organ preservation, fetal cardiac bypass, cancer treatment, and various areas of circulation research, which can be controlled in such a way as to produce a desired blood flow that closely approximates the physiological blood flow of the patient. The pump system includes a pulsating mechanism having a housing defining a chamber within which a compressible-expandable bladder is sealably mounted. The system further includes a hydraulic actuator having a pressure imparting member that acts upon a pressure transmissive fluid contained within the actuator chamber in a manner to generate a pulsatile pressure on the transmissive fluid, which, in turn, results in a pulsatile pressure being exerted on bladder in a manner to controllably vary the volume thereof. Additionally, the system includes a compact, highly reliable voice-coil motor that is operably associated with the hydraulic actuator for controllably moving the pressure imparting member within the fluid chamber and further includes a fully programmable motion controller that controls the voice-coil motor. Further, the system includes a programmable touch-screen component that functions to control the motion controller.

12 Claims, 12 Drawing Sheets

– – – "Typical" Pulse Wave Form
– ·· – ·· Stroke Volume Decreased
——— Upstroke Time Decreased
( More "Abrupt" ) Pulse Rate Increased

PHYSIOLOGIC PULSATILE PUMP

BACKGROUND OF THE INVENTION

1. Field of the Invention

The present invention relates generally to apparatus for providing extracorporeal circulation, cardiopulmonary bypass, ventricular assist (LVAD, RVAD, BiVAD), ECMO organ preservation, fetal cardiac bypass, cancer treatment, and various areas of circulation research. More particularly, the apparatus concerns an improved physiologic pulsatile pump system that accurately duplicates blood pressure and flow patterns with no abnormal hemolysis (blood damage).

2. Discussion of the Prior Art

The importance of inducing extracorporeal circulation which is as physiologic as possible has long been recognized. To Applicants' knowledge, the first and only physiologic pulsatile pump system was conceived in the mid-1950's by a heart surgeon named Selwyn Roy McCabe. During this time period Dr. McCabe was confronted by some children in a congenital heart ward. They asked "Doctor, are we going to live or die"? Realizing that with the then present technology there was little hope for the children, he commenced work on a physiologic tricuspid valve, which then evolved to a 2-chamber physiologic pulsatile pump with a number of unique features. The doctor also envisioned that such a system could allow quality time for corrective surgery, and ultimately, prolong life support. Dr. McCabe, who was also trained in internal cardiology and physiology, felt that accurate duplication of blood pressure and flow patterns could have significant advantages to both the major vital organs and to the microcirculation.

The physiologic total life support system conceived by Dr. McCabe was successfully tested on an adult dog in Bethesda, Md. in early 1957. A neonatal/infant model, The Pediatric Pulsatile Pump, was developed in the early '70's, and a number were sold for research purposes with very successful results. The present invention comprises a technologically significantly improved version of Dr. McCabe's system.

SUMMARY OF THE INVENTION

It is an object of the present invention to provide a pulsatile blood circulating pump system that is adapted for use in cardiopulmonary bypass, ventricular assist (LVAD, RVAD, BiVAD), ECMO, organ preservation, fetal cardiac bypass, cancer treatment, and various areas of circulation research.

Another object of the invention is to provide a pump system of the aforementioned character that can be controlled in such a way as to produce a desired blood flow that closely approximates the physiological blood flow of the patient.

Another object of the invention is to provide a pump system as described in the preceding paragraphs that includes a pulsating mechanism having a housing defining a chamber within which a compressible-expandable bladder is sealably mounted and further includes a hydraulic actuator having a pressure imparting chamber with a flexible diaphragm for generating a pulsatile pressure on the transmissive fluid. This, in turn, results in a pulsatile pressure being exerted on the bladder in a manner to controllably vary the volume thereof. Uniquely, a voice-coil actuator, including a compact, highly reliable voice-coil motor and motion controller is operably associated with the hydraulic actuator for controllably moving the pressure imparting member, here provided as a flexible diaphragm.

Another object of the invention is to provide a pump system as described in the previous paragraph that further includes a novel, fully programmable motion controller that controls the voice-coil motor.

Another object of the invention is to provide a pump system as described in the preceding paragraphs that further includes a programmable touch-screen component that functions to control the motion controller.

Another object of the invention is to provide a pump system of the character described that can be used in connection with cardiopulmonary bypass, ventricular assist (LVAD, RVAD, BiVAD), ECMO, organ preservation, fetal cardiac bypass, cancer treatment, and various areas of circulation research.

By way of summary, the foregoing objects, as well as other objects of the invention, are achieved by a physiologic pulsatile pump apparatus that includes a pulsatile flow pump that comprises a housing defining a chamber having an inlet port and a disposable, compressible-expandable bladder sealably mounted within the housing. The bladder, which has a receiving port and a delivery port is preferably formed from an advanced antithrombogenic material. The physiologic pulsatile pump apparatus also comprises a hydraulic actuator that is connected to the housing of the pulsatile flow pump. The hydraulic actuator, which includes a fluid chamber containing a pressure transmissive fluid, has an outlet port in communication with the inlet port of the pulsatile flow pump housing. A pressure imparting member is mounted within the fluid chamber for movement therewithin in a manner to generate a pulsatile pressure on the transmissive fluid so as to, in turn, cause a pulsatile pressure to be exerted on the bladder to controllably vary the volume thereof. A voice-coil motor is operably associated with the hydraulic actuator for controllably moving the pressure imparting member within the fluid chamber. Additionally, the physiologic pulsatile pump apparatus includes a fully programmable motion controller for controlling the voice-coil motor and a programmable touch-screen component that functions to control the motion controller.

DESCRIPTION OF THE INVENTION

Figure 1:
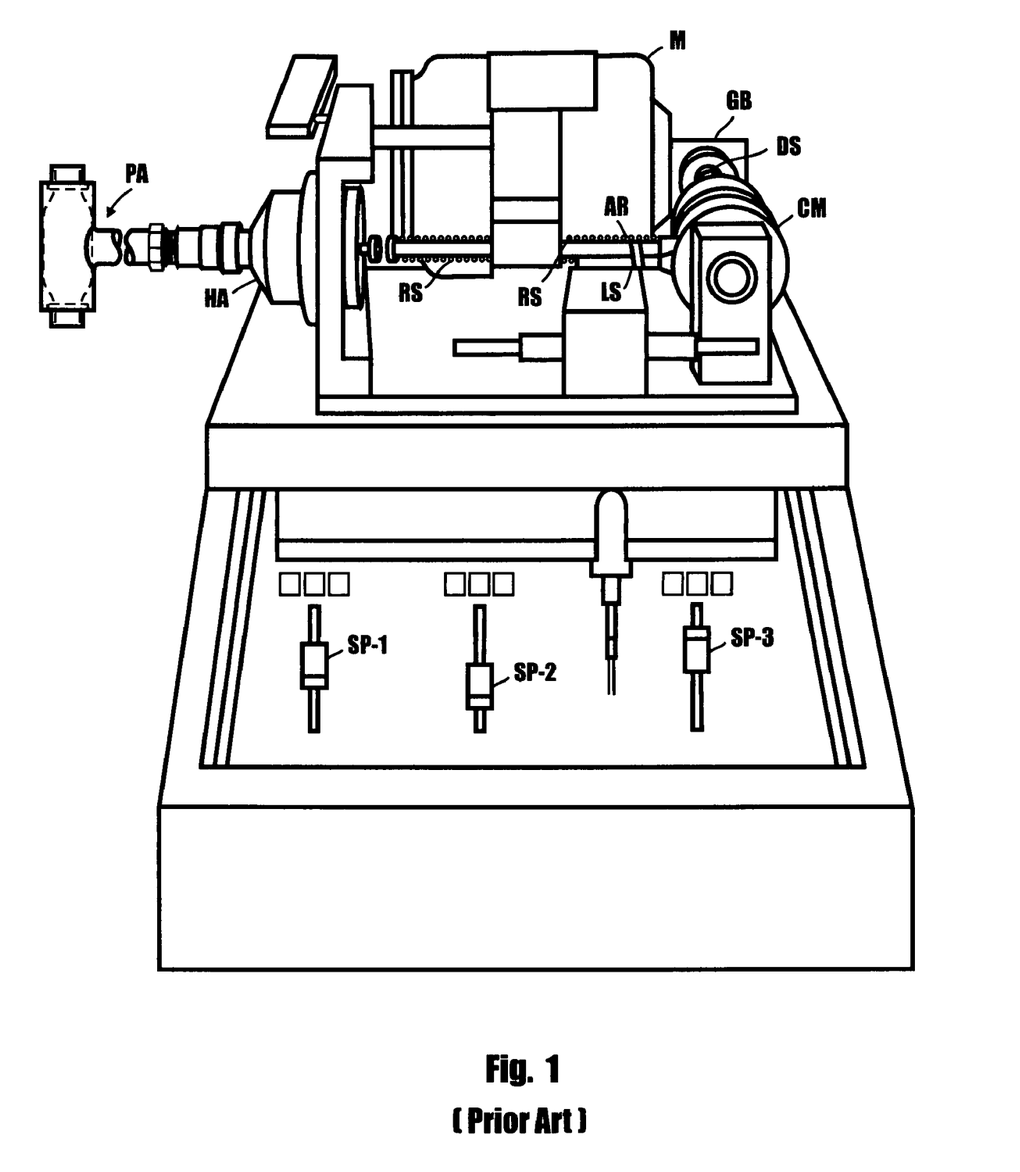
FIG. 1 is a generally perspective view of the prior art pulsatile pump apparatus developed by Dr. McCabe.
Figure 1A:
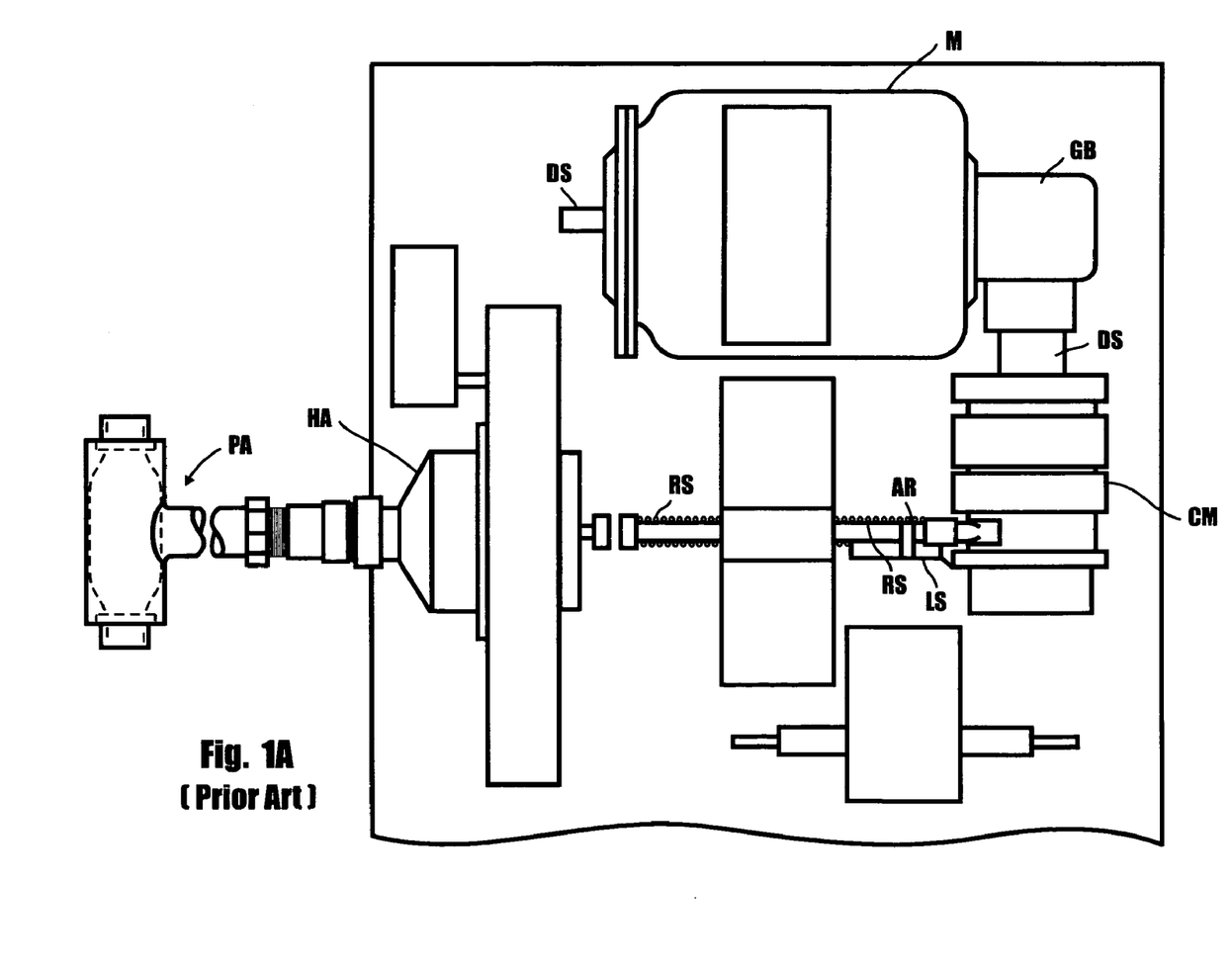
FIG. 1A is a fragmentary, top plan view of a portion of the prior art pulsatile pump apparatus developed by Dr. McCabe.
Figure 2:
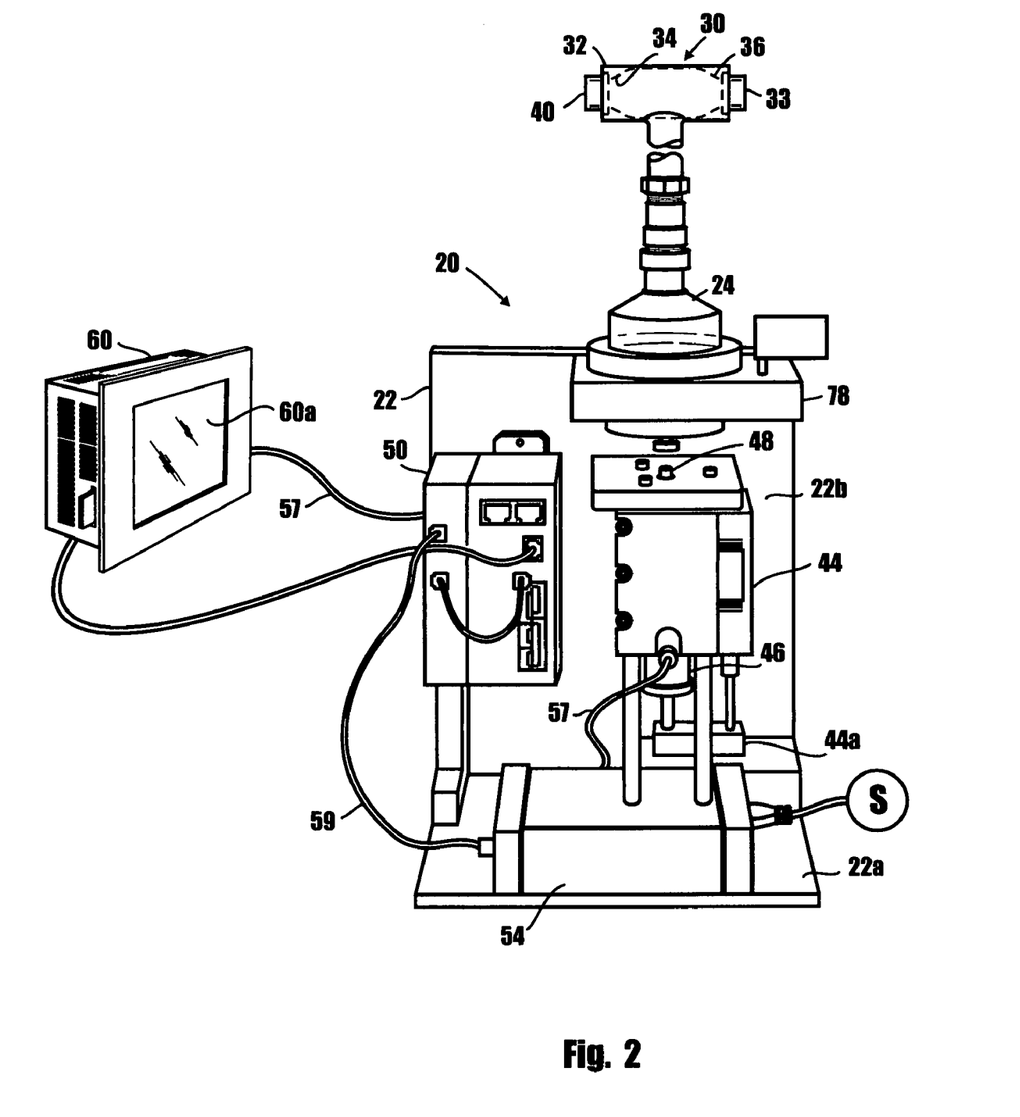
FIG. 2 is a generally perspective view of one form of the physiologic pulsatile pump system of the present invention.

Considering first the prior art system illustrated in FIG. 1 of the drawings, this system, which at the time of its development, represented a substantial advance in the art, exhibited numerous technological limitations not found in the vastly improved system of the present invention shown in FIG. 2 of the drawings. For example, the prior art system was analog and, therefore, not programmable. Further, the critical system variables, including pulse rate, stroke volume and upstroke-rise time were controlled by three separate slide potentiometers "SP-1," "SP-2" and "SP-3" with light emitting diode (LED) read-outs adapted to permit individual control of each variable. In practice, the LEDs were hard to read and, as they started to fail, frequently caused erroneous readings to occur. Further, in the prior art system, the pulse rate control required an additional three position multiplier switch to enable it to achieve the full range. Additionally, the slide potentiometer housing of the apparatus undesirably exhibited open space to the interior electronics which could permit fluids, including blood, to reach the interior of the control housing and thereby contaminate the electronics therewithin.

Because of the technological limitations inherent in the prior art system, response time, position control and operational accuracy were limited, trouble-shooting was tedious and diagnostic ability was quite limited.

From a mechanical standpoint, the prior art system as illustrated in FIG. 1 of the drawings was made up of components that were quite bulky, heavy and cumbersome to use and install. The motor "M" of the apparatus, which drove the hydraulic actuator "HA" of the system via a relatively complex clutch mechanism "CM", was a 90 Volt DC motor with brushes which required periodic maintenance. The drive shaft "DS" of the motor was interconnected with a gear box "GB" having a 40:1 gear ratio. Connected to the gearbox at a 90° angle was a custom shaft "DS". Mounted on the shaft "DS" was a custom-made concentric flywheel. Attached to the flywheel was a forwardly extending actuating rod "AR", which on its forward stroke drove the actuating piston of the hydraulic actuator, which was connected to the pump assembly "PA" of the apparatus. Operably associated with the actuating rod were two sets of return springs RS that functioned to return the actuating piston to its starting position upon the system electronics releasing the clutch mechanism. Attached to the clutch mechanism CM was an adjustable limit switch assembly "LS".

Undesirably, periodic maintenance of the prior art system was required because of continuous wear on the motor brushes, the gearbox and the clutch mechanism. Additionally, the gearbox required periodic maintenance. The clutch mechanism, which was exposed to air, could get dirty, at which time it would malfunction. A dust cover was made to cover the motor/clutch mechanism. Further, the clutch mechanism exhibited a limited life expectancy and replacement of the clutch mechanism would require time-consuming and expensive factory assistance.

Figure 7:
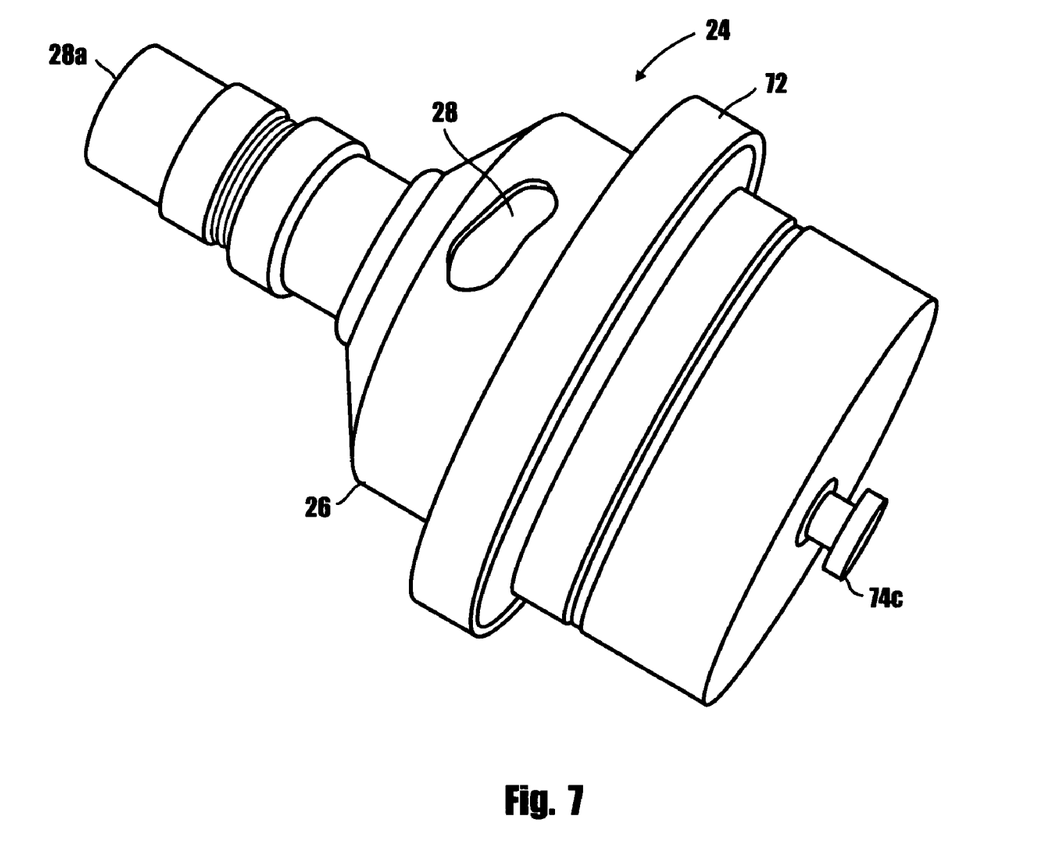
FIG. 7 is a generally perspective view of the hydraulic actuator sub-assembly of the apparatus shown in FIG. 2.
Figure 8:
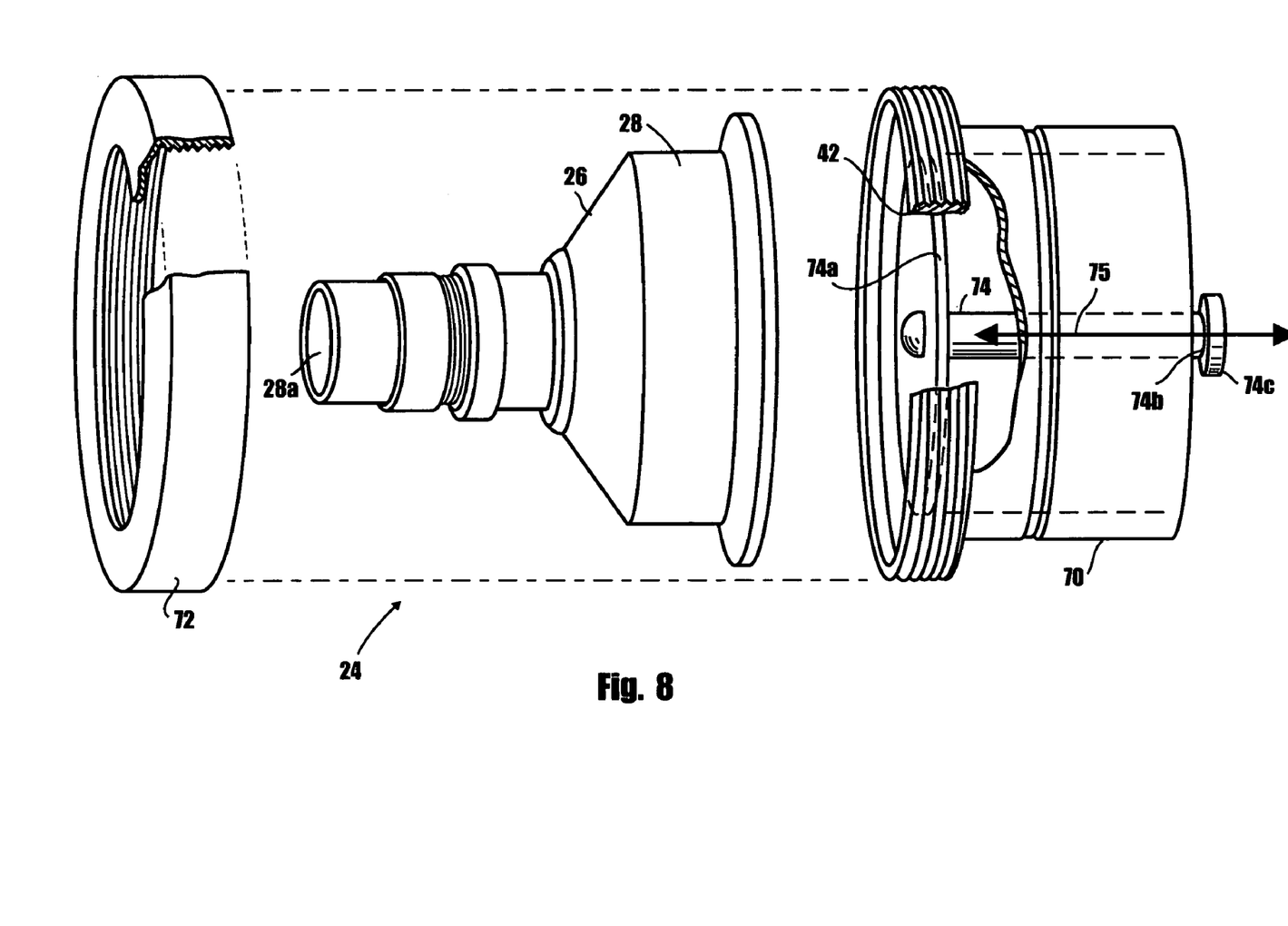
FIG. 8 is a generally perspective, exploded view of the hydraulic actuator sub-assembly shown in FIG. 7.

Referring now to FIG. 2 the drawings, one form of the physiologic pulsatile pump apparatus of the present invention is there illustrated and generally designated by the numeral 20. This apparatus, which is adapted primarily for use in cardiopulmonary bypass, ventricular assist (LVAD, RVAD, BiVAD), ECMO, organ preservation, fetal cardiac bypass, cancer treatment, and various areas of circulation research, here comprises a support assembly 22 having a base member 22a and a substantially vertical member 22b that is connected to the base member and extends therefrom. The voice-coil actuator motor has only one moving part, namely, a shaft moving through a bearing. These types of motors have been running in space applications for over 20 years of continuous operation, and their life expectancy is extended substantially when the motors are mounted in a vertical orientation. Connected to the vertical member 22b is a hydraulic actuator sub-assembly 24 having a housing 26 that defines a fluid chamber 28 having an outlet 28a (FIGS. 7 and 8). The function of this hydraulic actuator sub-assembly will presently be described.

Operably associated with the hydraulic actuator sub-assembly 24 is the important pulsatile flow pump 30 of the invention, which includes a fluid inlet port 30a that is in communication with outlet 28a of the hydraulic actuator sub-assembly in the manner shown in FIG. 2. As will be presently to be described in greater detail, pulsatile flow pump 30 in cooperation with the actuator sub-assembly 24 functions to generate a pulsatile blood flow that substantially duplicates that of the patient as recorded by a chart recorder.

Figure 9:
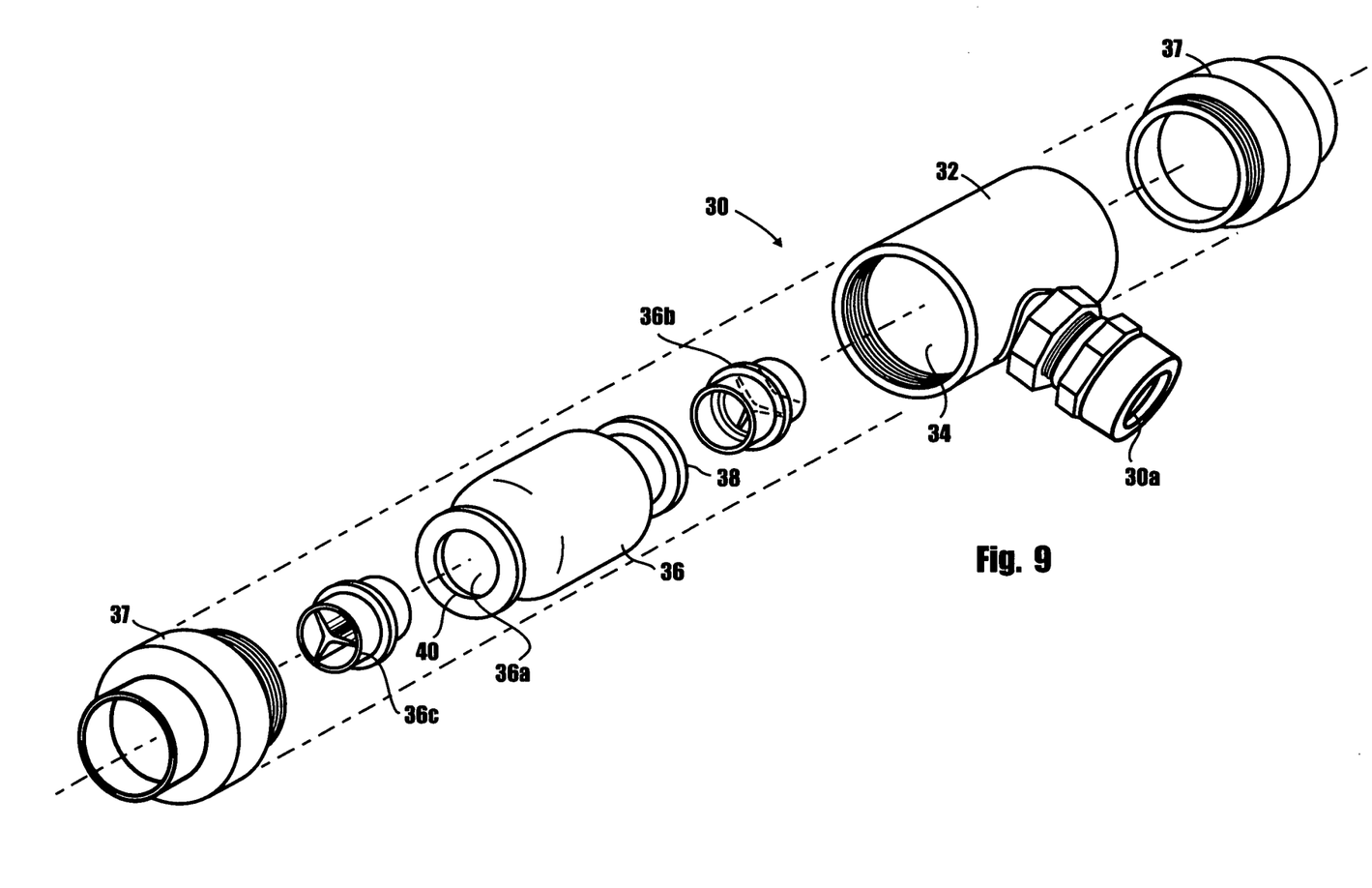
FIG. 9 is a generally perspective, exploded view of the pulsatile pump sub-assembly of the apparatus shown in FIG. 2.

As best seen by referring to FIGS. 2 and 9, mechanism 30 comprises a housing 32 defining a chamber 34 within which is mounted a disposable, compressible-expandable bladder 36 formed from an advanced, antithrobogenic, long-life material. Bladder 36 includes a bladder chamber 36a having a receiving port 38 and a delivery port 40, both of which are in communication with the patient "P" in the manner illustrated in FIG. 10.

As best seen in FIG. 8 of the drawings, sealably mounted within the fluid or actuator chamber 28 of the hydraulic actuator is an actuating member or diaphragm 42 that, during operation of the apparatus, acts upon a pressure transmissive fluid contained within the actuator chamber 28 in a manner to generate a pulsatile pressure on the transmissive fluid. As will be described in greater detail hereinafter, the pulsatile pressure generated on the transmissive fluid by the actuating member 42 results in a pulsatile pressure being exerted on bladder 36 in a manner to controllably vary the volume thereof.

Figures 5, 6:
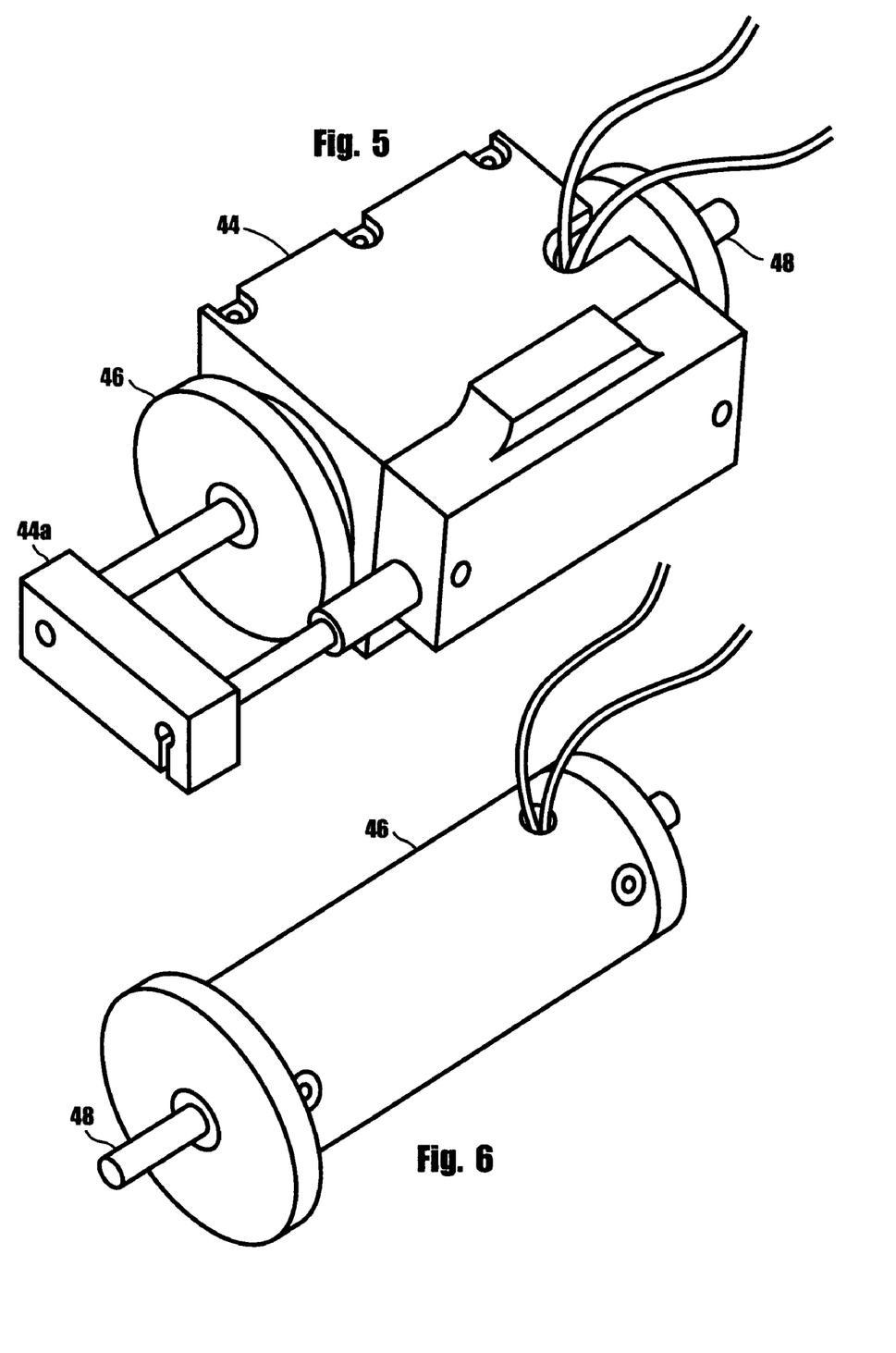
FIG. 5 is a generally perspective view of the voice-coil actuator sub-assembly of the apparatus shown in FIG. 2.
FIG. 6 is a generally perspective view of the voice-coil motor of the assembly shown in FIG. 5.

As will be discussed in greater detail hereinafter, operably associated with hydraulic actuator sub-assembly 24 is a voice-coil actuator assembly 44 (FIGS. 2 and 5) that functions to controllably move the actuating member 42 of the hydraulic actuator sub-assembly within the fluid chamber 28 thereof (See FIG. 8). Voice control actuator 44 includes a supporting frame 44a that is connected to substantially vertical member 22b and strategically supports a magnetic voice-coil motor 46 having a reciprocating shaft 48 (FIGS. 5 and 6). In a manner presently to be described, during operation of the apparatus, shaft 48 controllably acts upon actuator member 42 to create the pulsating flow. Voice-coil linear actuator, or motor 46, is readily commercially available from a number of sources, but an actuator offered for sale by H2W Technologies of Valencia, Calif. under the designation NCM10-15-020 and having a stroke of approximately 0.5" (½ inch) has proven quite satisfactory for present purposes. Motor 46, has numerous advantages over the motor of the prior art apparatus illustrated in FIG. 1 of the drawings, including being considerably smaller and lighter, being substantially safer and more reliable in operation, requiring no maintenance and advantageously readily controllable in much the same manner as a conventional servo-motor. Use of the voice-coil actuator 44 in the apparatus of the present invention advantageously eliminates the dual 90°-angled shafts, the concentric fly wheel, the gearbox, the difficult to service electromagnetic clutch, and return springs of the previously described prior art apparatus illustrated in FIG. 1.

Figure 4:
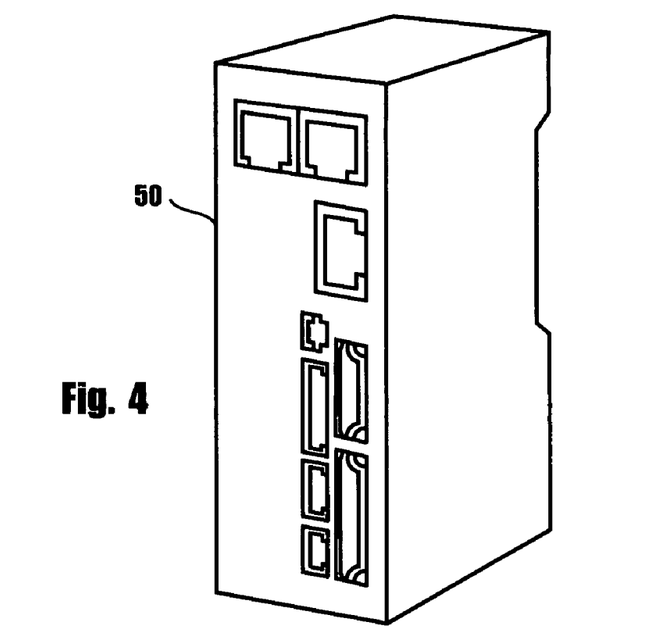
FIG. 4 is a generally perspective view of the programmable motion controller component of the apparatus shown in FIG. 2.

Also connected to vertical support member 22b of support 22 is a motion controller 50 that is operably associated with the voice-coil motor 46 for precisely controlling the motor (see FIGS. 2 and 4). Motion controller 50, which is of conventional construction, is readily available from several sources, including the Elmo USA Company of Westford, Mass. Motion controller 50, which comprises a readily programmable, state-of-the-art digital control system, provides closed-loop linear position control and utilizes RS-232 communication, which is a standard form of serial communication that is a recommended standard form of serial communication through a computer to control hardware such as the voice-coil actuator 46. Advantageously, motion controller 50 provides fast response time, accurate position control and permits remote trouble-shooting capability. Additionally, limit controls can be accurately programmed into the electronics of the controller with selected read-outs if desired, thereby providing a high degree of safety during operation of the apparatus of the invention.

When compared to the prior art apparatus shown in FIG. 1 of the drawings, it is abundantly clear that the use of motor controller 50 in the apparatus of the present invention provides substantially greater safety, greater reliability and superior compatibility with and control over cooperating operating components, such as the hydraulic actuator driving motor, the EKG-trigger and like peripherals.

As illustrated in FIG. 2 of the drawings, to provide electrical power to the motor 46 and to the motion controller 50, a conventional power supply 54 is suitably mounted on the horizontal member 22a of the support assembly 22 and is connected to a suitable source of power "S". Power supply 54 is readily commercially available from a number of sources, including the previously identified H2W Technologies of Valencia, Calif. Suitable cabling, including cables 57 and 59, interconnect the power supply with the motor 46 and the motion controller 50.

Figure 3:
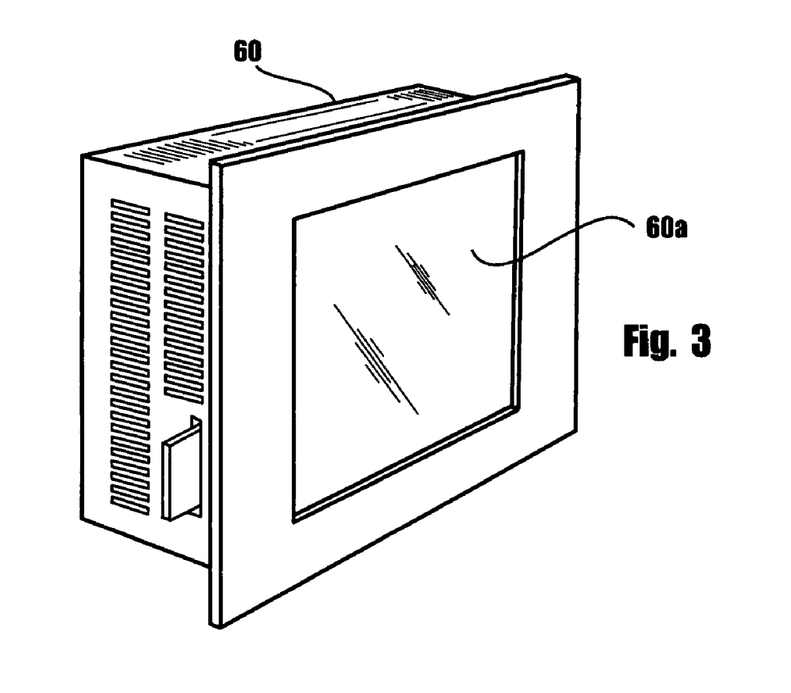
FIG. 3 is a generally perspective view of the touch-screen component of the apparatus shown in FIG. 2.

Operably associated with motion controller 50 via a connector 51 is a touch-screen unit 60 (FIGS. 2 and 3). Touch-screen unit 60, which includes desired color read-outs, is readily commercially available from a number of sources including the ESA Technology Company of Windsor, Calif. Touch-screen unit 60 here comprises a state-of-the-art touch-terminal that greatly simplifies the operation and control of the interactive components of the apparatus of the present invention. The touch-screen unit includes a rugged touch-screen 60a upon which graphic images in various formats, such as those illustrated in FIGS. 12 and 13 can be imported. During operation of the apparatus of the invention the read-outs on the touch-screen 60a that are easy to see can be quickly and precisely changed on-the-fly and, in a manner presently to be discussed, automatically activates with an EKG signal. When compared with the apparatus of the prior art as illustrated in FIG. 1 of the drawings, the apparatus of the present invention that includes the cooperatively associated motion controller 50 and the touch-screen unit 60 permits significantly greater control of pulse rate, stroke volume, and upstroke-rise time as well as providing much more precise resolution.

The apparatus of the invention as described in the preceding paragraphs is designed to accurately duplicate a blood pressure curve by independently varying pulse rate, that is the number of beats per minute; stroke volume, that is the volume of blood pumped on each beat and upstroke-rise time, that is the duration of time from the start to peak pressure at the top of the curve on each beat. In a potential clinical application, as, for example, a cardiopulmonary bypass procedure or an organ preservation procedure, this duplication of the blood pressure curve can be achieved by one form of the method of the invention that includes the following steps. The first step in the process is to obtain in a conventional manner a blood pressure chart recorder tracing from the patient or organ being treated. The dotted lines 63 of FIG. 11 of the drawings, which is a plot of pressure versus time, illustrates a typical pulse wave-form. Using this information, the pulse rate and upstroke-rise time can be calculated and programmed into the touch-screen unit 60 in a manner well understood by those skilled in the art (see FIGS. 12 and 13). The dotted lines 65 of FIG. 11 of the drawings illustrate a stroke volume decrease, while the solid line 67 illustrates a decrease in upstroke time.

With the forgoing in mind, the basic design theory of the apparatus of the invention is that once the pulse wave and flow patterns are duplicated, pressure and flow will be controlled by the peripheral resistance of the blood vessels, there will be no variance in blood pressure/flow patterns; the capillary beds (microcirculation) will be filled and flushed with a full flow of blood; there will be normal oxygenation of all tissues; and all waste products (metabolites) will be effectively removed. In addition, the pulsatile flow created by the apparatus of the present invention has been proven to be vastly superior to non-pulsatile flow and non-physiologic "pulsatile flow" created by other types of prior art apparatus. More particularly, based on a study of 194 related articles published between 1952 and 2006, it has been determined that pulsatile flow decreased the incidence of post-operative deaths in pediatric and adult patients, significantly improved blood flow of vital organs including brain, heart, liver, and pancreas, reduced systemic inflammatory response syndrome, significantly improved vital organ recovery in several types of animal models when compared to non-pulsatile perfusion and generates more hemodynamic energy, which better maintains the microcirculation compared with non-pulsatile flow. It has also been determined that infants receiving pulsatile blood flow during bypass surgery awakened more quickly, were more alert and required less post-operative ventilation.

In order to ready the apparatus of the invention to permit accomplishment of the method of the invention, the various components of the apparatus are assembled together in a manner illustrated in FIG. 2 of the drawings. In this regard, the hydraulic actuating unit 24 is first assembled in the manner indicated in FIG. 8 of the drawings by operably interconnecting the housing 26 with the actuator base 70 using the threaded connector ring 72. Actuator base 70 houses the previously mentioned diaphragm 42 which is interconnected with an operating shaft 74 that is reciprocally movable within base 70 in the manner indicated by the arrow 75 of FIG. 8. Next, the assembled actuating unit 24 is mounted within a capture plate 78 that is interconnected with vertical support member 22b in the manner shown in FIG. 2 of the drawings. This done, the fluid reservoir, or chamber 28 of the actuating unit is filled with a suitable pressure transmissive fluid.

With the actuating unit 24 properly mounted on the support structure in the manner shown in FIG. 2, the pulsatile flow pump 30 is interconnected with the actuating unit so that the inlet 30a of the mechanism is in fluid communication with outlet 28a of the actuating unit and is in fluid communication with the fluid reservoir or chamber 28 of the actuating unit.

Figures 10, 11:
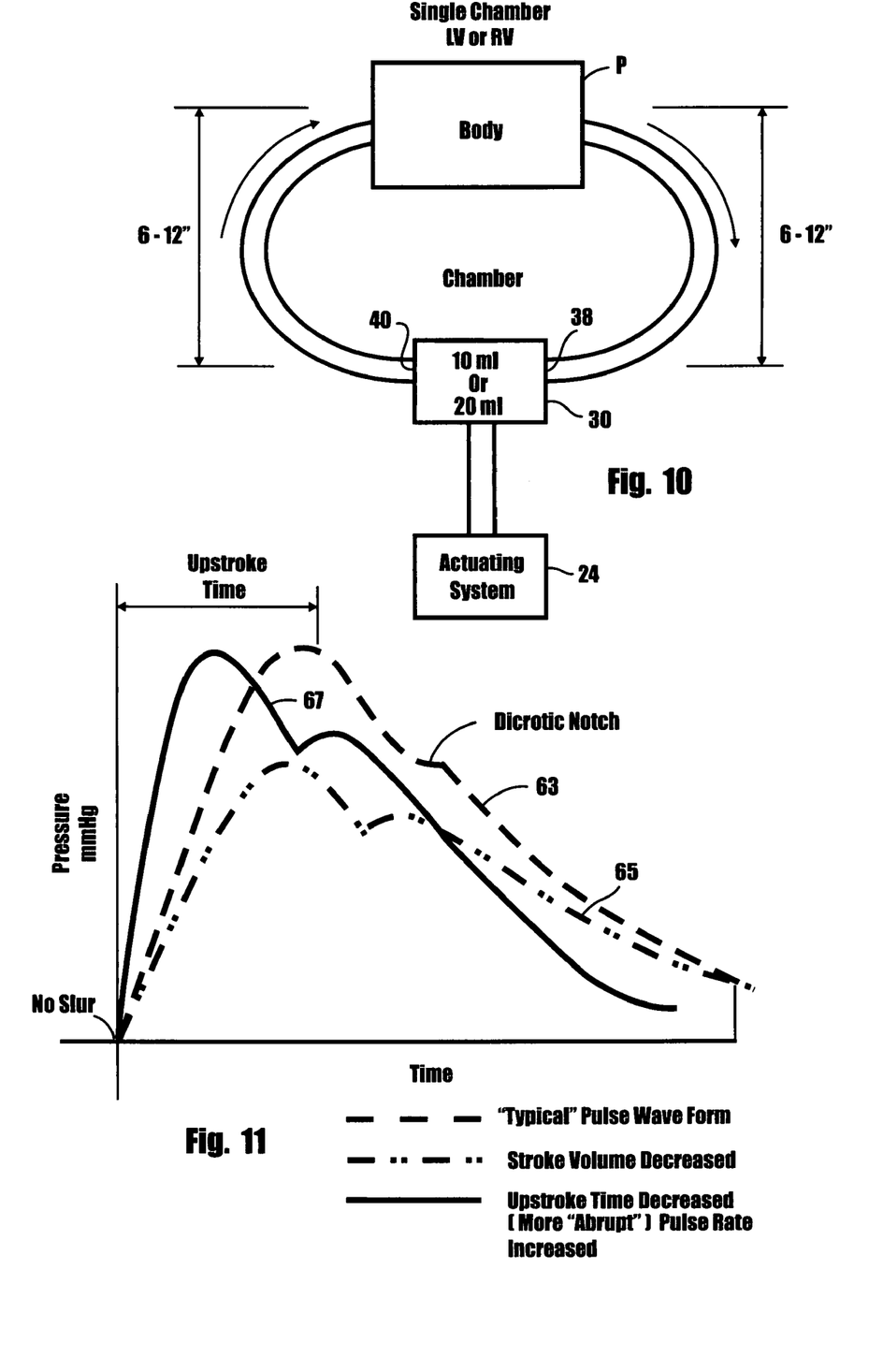
FIG. 10 is a generally diagrammatic view illustrating the manner of interconnection of the hydraulic actuator sub-assembly and the pulsatile pump sub-assembly with the patient.
FIG. 11 is a generally diagrammatic view illustrating a set of typical blood-pressure curves.

As previously mentioned, and as indicated in FIGS. 2 and 9 of the drawings, the compressible-expandable bladder 36 of the pulsatile flow pump is centrally disposed within chamber 34 of housing 32 so that the receiving and delivery ports 38 and 40 thereof extend outwardly from housing 32 to enable them to be interconnected with the patient in the manner illustrated in FIG. 10.

Figure 12:
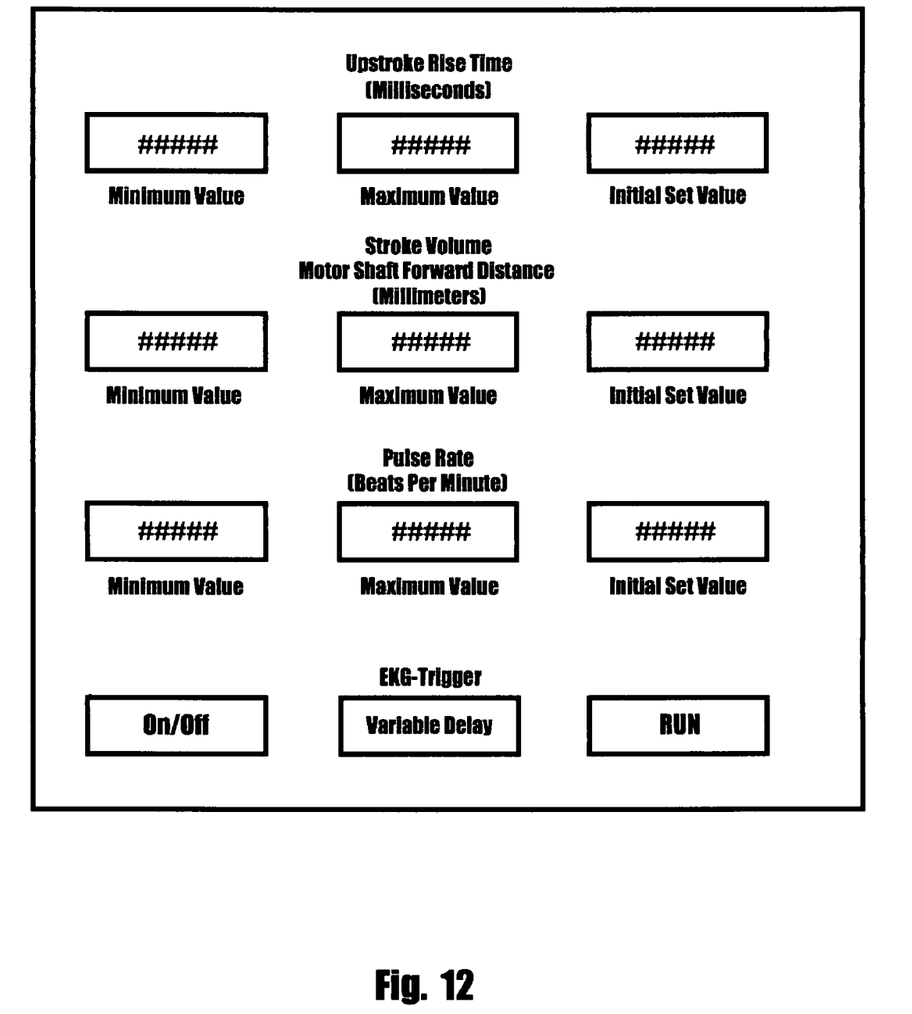
FIG. 12 is a generally diagrammatic view illustrating one type of image that appears on the touch-screen sub-assembly of the apparatus.
Figure 13:
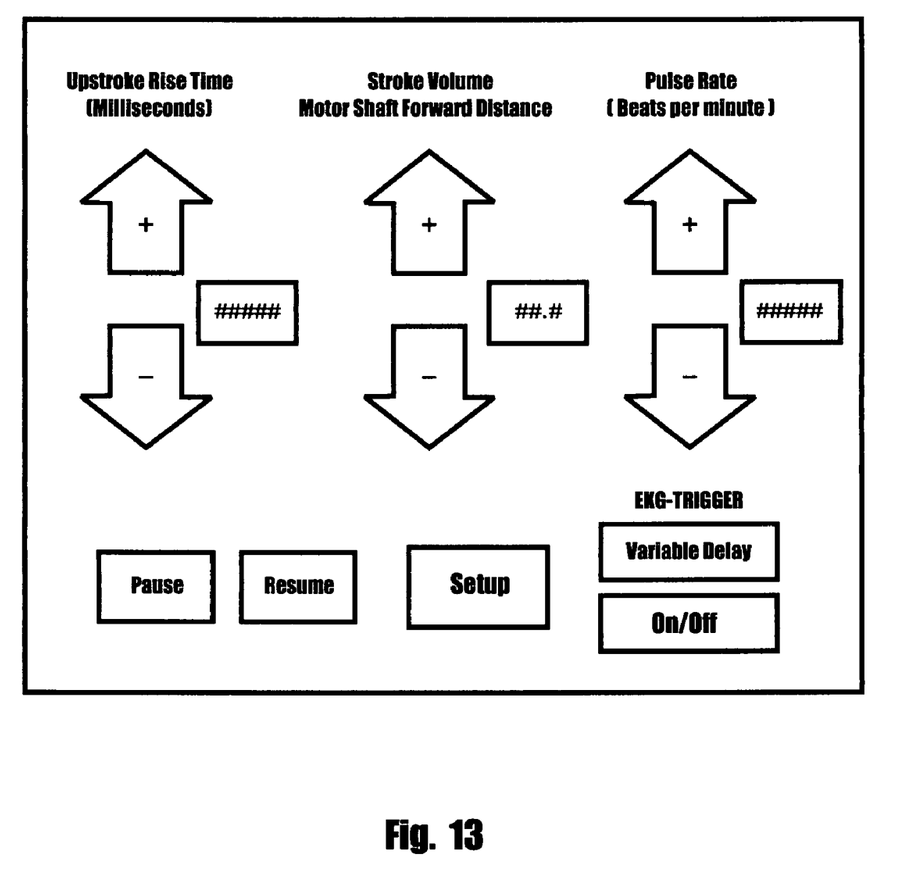
FIG. 13 is a generally diagrammatic view illustrating another type of image that appears on the touch-screen sub-assembly of the apparatus.

Following the programming of the motion controller and the touch-screen unit in a manner well understood by those skilled in the art, the pumping or perfusion step is commenced by manipulating the stroke volume control image appearing on the touch-screen in a manner such that the blood pressure curve matches the chart recorder blood pressure reading obtained from the patient (see for example FIGS. 12 and 13). Other applications such as ventricular assist (LVAD, RVAD, BiVAD), ECMO, etc., may have different perfusion requirements, and the system of the present invention is uniquely able to adapt to each application.

As previously mentioned, the pumping or perfusion step is accomplished by the cooperative interaction of the hydraulic actuator sub-assembly 24 and the pulsatile flow pump 30 of the invention. In this regard, as illustrated in FIG. 8, the hydraulic actuator sub-assembly 24 includes a reciprocating shaft 74 that is interconnected with diaphragm 42 at one extremity 74a and has, at its other extremity 72b, an enlarged diameter head portion 74c that is acted upon by shaft 48 of the voice control motor 46 as the motor shaft reciprocates under the control of the motion controller 50.

As shaft 74 of the actuator sub-assembly 24 reciprocates, diaphragm 42 acts upon a pressure transmissive fluid contained within the actuator chamber 28 in a manner to generate a pulsatile pressure on the transmissive fluid. The pulsatile pressure generated on the transmissive fluid in turn results in a pulsatile pressure being exerted on bladder 36 in a manner to controllably vary the volume thereof. More particularly, as the bladder 36 is collapsed by the pressure exerted on the bladder by the pressure transmissive fluid, blood is forced outwardly of the delivery port 40 of the bladder 36 and through the novel tricuspid valves 36b that is mounted within the delivery port (FIG. 9). Conversely, a reduction in pressure of the transmissive fluid caused by a retraction of the reciprocating shaft 48 permits the compressible-expandable bladder 36 to expand in a manner to allow highly desirable positive pressure/passive infilling via the inflow or receiving port 38 via the tricuspid valve 36c that is mounted within the port (See FIGS. 9 and 10).

Tricuspid valves 36b and 36c, which are held in position by threaded connectors 37, uniquely mimic the shape and action of the native tricuspid heart valve which is located on the right side of the heart between the right atrium and the right ventricle. During normal operation of the heart, the right atrium receives deoxygenated blood from the superior and inferior vena cavae and the coronary sinus and pumps it into the right ventricle through the heart's tricuspid valve.

Continued operation of the pulsatile flow pump 30, the hydraulic actuator sub-assembly 24 and voice-coil motor 46, which is under the control of the motion controller 50, will generate a physiologic pulsatile blood flow that very accurately duplicates blood pressure and flow patterns of the patient while handling the patient's blood gently.

When the apparatus of the invention is used to partially support a beating heart in carrying out procedures such as Ventricular Assist and Extracorporeal Membrane Oxygen-ation (ECMO), the proper timing of each beat of the pump is vital. In this regard, medical research has shown that a pump system that is assisting a beating heart needs to trigger shortly after the actual heart beat. Pumping at the same time actually puts an additional load on the heart. The Variable Delay allows the exact desired time interval to be set which gives optimal healing. Each beat shows two pressure peaks on the monitor.

Figure 14:
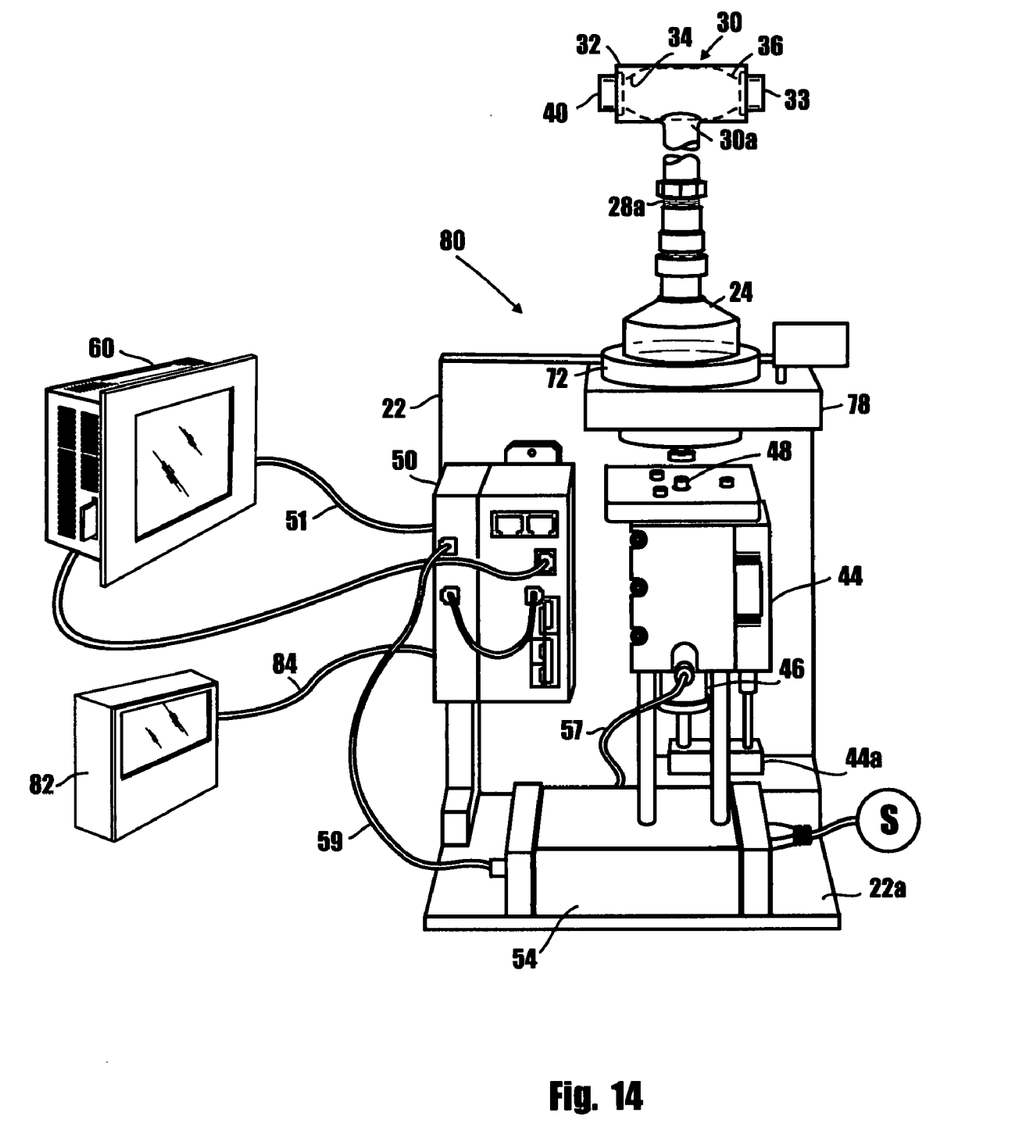
FIG. 14 is a generally perspective view of an alternate form of physiological pulsatile pump system of the present invention.

In accomplishing the procedures identified in the preceding paragraph, an alternate form of the apparatus of the invention is used. This alternate form of the apparatus of the invention, which is illustrated in FIG. 14 of the drawings and is generally designated by the numeral 80, uniquely includes an EKG trigger circuit. This alternate form of the apparatus is similar in most respects to that illustrated in FIGS. 2 through 13 and like numerals are used in FIG. 14 to identify like components. In the apparatus of this latest form of the invention, an EKG unit 82 is interconnected with the motion controller 50 by means of a suitable cable 84. With this construction, during the accomplishment of the operational procedure, the system can be triggered by an electronic EKG signal obtained from the patient's heart so that that the mechanism 30 beats every time the patient's heart beats. In some laboratory studies, when a heart was removed and placed on an oxygen preservation perfusion machine, the heart continued to beat out of the body (ex vivo). That application would also require an EKG-trigger with a Variable Delay. In this alternate form of the apparatus, when the EKG-trigger is activated, the trigger uniquely overrides the Pulse Rate Control on the Touch-screen 60 (see FIG. 13). In the present invention, the EKG-trigger and Variable Delay are built-in to the electronics, and are controlled on the touch-screen with read-outs. In the prior art system, the EKG unit was a later "add-on", and thus was an additional external circuit which acted as a relay between patient and the pump system. In the prior art unit there were more cords, no read-out of the delay and the unit could only be activated by flipping a switch on the back of the pump as compared to an automatic override on the new system.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A physiologic pulsatile pump apparatus comprising:
   (a) a housing defining a chamber having an inlet port;
   (b) a disposable, compressible-expandable bladder sealably mounted within said housing, said bladder having a receiving port and a delivery port;
   (c) an hydraulic actuator connected to said housing, said the hydraulic actuator comprising:
      (i) a fluid chamber containing a pressure transmissive fluid, said fluid chamber having an outlet port in communication with said inlet port of said housing; and
      (ii) an actuating member mounted within said fluid chamber for movement within said fluid chamber in a manner to generate a pulsatile pressure on said transmissive fluid so as to cause a pulsatile pressure on said bladder to vary the volume thereof; and
   (d) a voice-coil motor operably associated with said hydraulic actuator for controllably moving said actuating member within said fluid chamber, said voice-coil motor including a reciprocally movable shaft having an extremity in communication with said actuating member of said hydraulic actuator for imparting movement to said actuating member.

2. The apparatus as claimed in claim 1 in which said reciprocally movable shaft has a stroke of approximately 0.5" (½ inch).

3. The apparatus is defined in claim 1, further including a support assembly having a base member and a substantially vertical member connected to said base member and extending therefrom, said voice-coil motor being interconnected with said vertical member.

4. The apparatus as defined in claim 2, further including a motion controller operably associated with said voice-coil motor for controlling said motor.

5. The apparatus as defined in claim 4, further including a touch-screen operably associated with said motion controller for controlling said motion controller.

6. The apparatus as defined in claim 5, further including an EKG trigger operably associated with said motion controller.

7. An apparatus for use in the cardiopulmonary bypass, ventricular assist (LVAD, RVAD, BiVAD), ECMO, organ preservation, fetal cardiac bypass, cancer treatment, and various areas of circulation research comprising:
 (a) a support assembly having a base member and a substantially vertical member connected to said base member and extending therefrom;
 (b) a hydraulic actuator sub-assembly connected to said vertical member of said support, said hydraulic actuator sub-assembly comprising a fluid chamber having an outlet and an actuating member movable within said fluid chamber;
 (c) a voice-coil motor operably associated with said actuating member of said hydraulic actuator sub-assembly for controllably moving said actuating member within said fluid chamber;
 (d) a pulsating mechanism connected to said fluid outlet of said hydraulic actuator sub-assembly, said pulsating mechanism comprising a housing and a compressible-expandable bladder disposed within said housing, said bladder being formed from an anti-coagulative material and having an inlet in an outlet in communication with the patient;
 (e) a motion controller operably associated with said voice-coil motor for controlling movement thereof;
 (f) a power supply mounted on said base member of said support and operably interconnected with said motion controller; and
 (g) a touch-screen operably associated with said motion controller for controlling said motion controller.

8. The apparatus as defined in claim 7, further including a tricuspid valve mounted within each of said receiving and delivery ports of said bladder.

9. The apparatus as claimed in claim 7 in which said voice-coil motor includes a reciprocally movable shaft having an extremity in communication with said actuating member of said hydraulic actuator for imparting movement to said actuating member.

10. The apparatus as claimed in claim 9 in which said reciprocally movable shaft has a stroke of approximately 0.5 inch (½ inch).

11. An apparatus for use in the cardiopulmonary bypass, ventricular assist (LVAD, RVAD, BiVAD), ECMO, organ preservation, fetal cardiac bypass, cancer treatment, and various areas of circulation research comprising:
 (a) a support assembly having a base member and a substantially vertical member connected to said base member and extending therefrom;
 (b) an hydraulic actuator sub-assembly connected to said vertical member of said support, said hydraulic actuator sub-assembly comprising a fluid chamber having an outlet and an actuating member movable within said fluid chamber;
 (c) a voice-coil motor operably associated with said actuating member of said hydraulic actuator sub-assembly for controllably moving said actuating member within said fluid chamber, said voice-coil motor having a reciprocally movable shaft in communication with said actuating member of said hydraulic actuator for imparting movement to said actuating member;
 (d) a pulsating mechanism connected to said fluid outlet of said hydraulic actuator sub-assembly, said pulsating mechanism comprising a housing and a compressible-expandable bladder disposed within said housing, said bladder being formed from an anti-coagulative material and having an inlet in an outlet in communication with the patient;
 (e) a tricuspid valve mounted within said delivery port of said bladder;
 (f) a motion controller operably associated with said voice-coil motor for controlling movement thereof;
 (g) a power supply mounted on said base member of said support and operably interconnected with said motion controller; and
 (h) a touch-screen operably associated with said motion controller for controlling said motion controller.

12. A physiologic pulsatile pump apparatus comprising:
 (a) a housing defining a chamber having an inlet port;
 (b) a disposable, compressible-expandable bladder sealably mounted within said housing, said bladder having a receiving port and a delivery port;
 (c) an hydraulic actuator connected to said housing, said the hydraulic actuator comprising:
  (i) a fluid chamber containing a pressure transmissive fluid, said fluid chamber having an outlet port in communication with said inlet port of said housing; and
  (ii) an actuating member mounted within said fluid chamber for movement within said fluid chamber in a manner to generate a pulsatile pressure on said transmissive fluid so as to cause a pulsatile pressure on said bladder to vary the volume thereof; and
 (d) a voice-coil motor operably associated with said hydraulic actuator for controllably moving said actuating member within said fluid chamber; and
 (e) a tricuspid valve mounted within said delivery port of said bladder and a tricuspid valve mounted within said receiving port of said bladder.

* * * * *